(12) United States Patent
Dale et al.

(10) Patent No.: US 7,282,182 B2
(45) Date of Patent: Oct. 16, 2007

(54) SAMPLE CARRIER

(75) Inventors: James D. Dale, Nashua, NH (US);
Gerard J. Sevigny, Nashua, NH (US);
Matthew W. Webb, Del Mar, CA (US);
Gus G. Tseo, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 798 days.

(21) Appl. No.: 10/199,690

(22) Filed: Jul. 18, 2002

(65) Prior Publication Data

US 2003/0017084 A1  Jan. 23, 2003

Related U.S. Application Data

(60) Provisional application No. 60/307,047, filed on Jul. 20, 2001.

(51) Int. Cl.
*B01L 9/06* (2006.01)
(52) U.S. Cl. ..................................... 422/104
(58) Field of Classification Search .............. 422/104, 422/64
See application file for complete search history.

(56) References Cited

U.S. PATENT DOCUMENTS

| | | | |
|---|---|---|---|
| 143,417 A | 10/1873 | Munroe | |
| 418,940 A | 1/1890 | Bray | |
| 1,168,535 A | 1/1916 | Moltrum | |
| 1,168,585 A * | 1/1916 | Moltrum | 172/783 |
| 1,549,111 A | 8/1925 | Grollman | |
| 1,634,953 A * | 7/1927 | McCune et al. | 211/13.1 |
| D110,691 S * | 8/1938 | Dudley | D9/753 |
| 2,467,873 A | 4/1949 | Weir | |
| 2,708,037 A | 5/1955 | Planeta | |
| 2,741,913 A | 4/1956 | Dovas | |
| 2,902,170 A | 9/1959 | Miller | |
| 2,956,686 A | 10/1960 | Garey | |
| 2,979,210 A | 4/1961 | Patterson | |
| 3,072,362 A | 1/1963 | Allen | |
| 3,109,084 A | 10/1963 | Walsh | |
| 3,115,247 A | 12/1963 | Hauser | |

(Continued)

FOREIGN PATENT DOCUMENTS

EP    0919281 A2    6/1999

(Continued)

*Primary Examiner*—Jill Warden
*Assistant Examiner*—Natalia Levkovich
(74) *Attorney, Agent, or Firm*—Charles B. Cappellari

(57) ABSTRACT

A sample carrier comprising a top wall, a base, and a support wall joining the top wall and the base. The top wall includes aligned, spaced-apart openings on at least one side of the support wall which are sized to receive sample tubes. Sleeves depending from the top wall and circumscribing each opening direct sample tubes into sample tube holding areas. The sample tube holding areas each include one or more retaining walls extending upward from the base opposite the support wall. Springs extending outward from the support wall bias sample tubes against the retaining walls. A drip shield comprising a cover plate, a pair of through-holes for accessing sample tubes in the sample carrier, and a depending fin which separates sample tubes on opposite sides of the support wall protects against cross-contamination between sample tubes held by the sample carrier.

24 Claims, 13 Drawing Sheets

U.S. PATENT DOCUMENTS

| | | |
|---|---|---|
| 3,142,385 A | 7/1964 | Kahlenberg |
| 3,175,695 A | 3/1965 | Goodman et al. |
| 3,186,556 A | 6/1965 | Forsstrom |
| 3,375,934 A | 4/1968 | Bates |
| 3,390,783 A | 7/1968 | Quakenbush, Jr. |
| 3,474,913 A | 10/1969 | Jungner et al. |
| D216,491 S | 1/1970 | Brown |
| 3,605,829 A | 9/1971 | Genese et al. |
| 3,643,812 A | 2/1972 | Mander et al. |
| 3,680,967 A | 8/1972 | Englehardt |
| 3,698,563 A | 10/1972 | Gordon et al. |
| 3,744,661 A | 7/1973 | Fischer, Jr. |
| 3,752,651 A | 8/1973 | Bush |
| 3,765,538 A | 10/1973 | Kowert |
| 3,785,773 A | 1/1974 | Rohrbaugh |
| RE28,165 E | 9/1974 | McCormick |
| 3,904,035 A | 9/1975 | Metzler et al. |
| 3,905,482 A | 9/1975 | Knulst |
| 3,905,772 A | 9/1975 | Hartnett et al. |
| 3,909,203 A | 9/1975 | Young et al. |
| 3,960,271 A | 6/1976 | Nelson |
| 4,036,391 A | 7/1977 | Prodel |
| 4,043,762 A | 8/1977 | Olds |
| 4,055,396 A | 10/1977 | Meyer et al. |
| 4,124,122 A | 11/1978 | Emmitt |
| 4,160,803 A | 7/1979 | Potts |
| 4,202,634 A | 5/1980 | Kraft et al. |
| 4,207,289 A | 6/1980 | Weiss |
| 4,265,855 A | 5/1981 | Mandle et al. |
| 4,284,603 A | 8/1981 | Korom |
| 4,287,155 A | 9/1981 | Tersteeg et al. |
| 4,322,216 A | 3/1982 | Lillig et al. |
| D265,126 S | 6/1982 | Beall |
| 4,391,780 A | 7/1983 | Boris |
| 4,407,943 A | 10/1983 | Cole et al. |
| 4,422,555 A | 12/1983 | Jacobs |
| 4,434,890 A | 3/1984 | Sieck et al. |
| 4,438,068 A | 3/1984 | Forrest |
| 4,495,150 A | 1/1985 | Cook et al. |
| 4,510,119 A | 4/1985 | Hevey |
| 4,522,089 A | 6/1985 | Alvi |
| D280,130 S | 8/1985 | Harkins et al. |
| 4,534,465 A | 8/1985 | Rothermel et al. |
| D286,912 S | 11/1986 | Andersen |
| 4,639,135 A | 1/1987 | Borer et al. |
| D290,401 S | 6/1987 | Bjorkman |
| 4,751,052 A | 6/1988 | Schwartz et al. |
| 4,761,268 A | 8/1988 | Andersen et al. |
| 4,787,523 A | 11/1988 | Kalous |
| 4,805,772 A | 2/1989 | Shaw et al. |
| 4,824,641 A | 4/1989 | Williams |
| 4,849,177 A | 7/1989 | Jordan |
| 4,895,650 A | 1/1990 | Wang |
| 4,932,533 A | 6/1990 | Collier |
| 4,933,147 A | 6/1990 | Hollar et al. |
| 4,948,564 A | 8/1990 | Root et al. |
| 4,963,493 A | 10/1990 | Daftsios |
| 4,982,850 A | 1/1991 | Mears |
| 5,004,103 A | 4/1991 | Connors et al. |
| 5,006,066 A | 4/1991 | Rouse |
| 5,029,699 A | 7/1991 | Insley et al. |
| 5,057,282 A | 10/1991 | Linder |
| 5,077,013 A | 12/1991 | Guigan |
| 5,080,232 A | 1/1992 | Leoncavallo et al. |
| 5,082,631 A | 1/1992 | Lenmark, Sr. et al. |
| 5,098,663 A | 3/1992 | Berthold et al. |
| 5,108,287 A | 4/1992 | Yee et al. |
| 5,127,541 A | 7/1992 | Wakatake |
| 5,128,105 A | 7/1992 | Berthold et al. |
| 5,133,939 A | 7/1992 | Mahe |
| 5,137,693 A | 8/1992 | Mawhirt |
| 5,169,603 A | 12/1992 | Landsberger |
| 5,173,265 A | 12/1992 | Golias et al. |
| D333,522 S | 2/1993 | Gianino |
| 5,186,339 A | 2/1993 | Heissler |
| 5,191,975 A | 3/1993 | Pezzoli et al. |
| D336,219 S | 6/1993 | Held |
| 5,217,694 A | 6/1993 | Gibler et al. |
| 5,232,669 A | 8/1993 | Pardinas |
| 5,318,753 A | 6/1994 | Honda |
| 5,322,668 A * | 6/1994 | Tomasso ..................... 422/104 |
| 5,324,481 A | 6/1994 | Dunn et al. |
| 5,350,564 A | 9/1994 | Mazza et al. |
| 5,378,433 A | 1/1995 | Duckett et al. |
| 5,456,360 A | 10/1995 | Griffin |
| 5,456,882 A | 10/1995 | Covain |
| 5,472,669 A | 12/1995 | Miki et al. |
| 5,533,700 A | 7/1996 | Porter |
| 5,571,481 A | 11/1996 | Powell et al. |
| 5,579,928 A | 12/1996 | Anukwuem |
| 5,632,388 A | 5/1997 | Morrison et al. |
| 5,642,816 A | 7/1997 | Kelly et al. |
| 5,650,125 A | 7/1997 | Bosanquet |
| 5,651,941 A | 7/1997 | Stark et al. |
| 5,687,849 A | 11/1997 | Borenstein et al. |
| 5,700,429 A | 12/1997 | Buhler et al. |
| 5,704,495 A | 1/1998 | Bale et al. |
| 5,777,303 A | 7/1998 | Berney |
| D405,192 S | 2/1999 | Smith et al. |
| 5,897,090 A | 4/1999 | Smith et al. |
| 5,916,527 A | 6/1999 | Haswell |
| 5,931,318 A | 8/1999 | Shauo |
| D413,677 S | 9/1999 | Dumitrescu et al. |
| D414,273 S | 9/1999 | Smith et al. |
| 5,959,221 A * | 9/1999 | Boyd et al. .............. 73/864.24 |
| D417,009 S | 11/1999 | Boyd |
| 5,985,219 A | 11/1999 | Lind |
| 5,993,745 A | 11/1999 | Laska |
| 5,996,818 A | 12/1999 | Boje et al. |
| 6,015,534 A | 1/2000 | Atwood |
| D420,747 S * | 2/2000 | Dumitrescu et al. ........ D24/227 |
| D421,130 S | 2/2000 | Cohen et al. |
| 6,027,691 A * | 2/2000 | Watts et al. .................. 422/64 |
| 6,065,617 A | 5/2000 | Cohen et al. |
| 6,123,205 A | 9/2000 | Dumitrescu et al. |
| D433,759 S * | 11/2000 | Mathis et al. .............. D24/227 |
| 6,156,275 A * | 12/2000 | Dumitrescu et al. ........ 422/104 |
| 6,190,619 B1 | 2/2001 | Kilcoin et al. |
| 6,193,064 B1 | 2/2001 | Finneran |
| D439,673 S | 3/2001 | Brophy et al. |
| 6,221,317 B1 | 4/2001 | Carl |
| 6,235,245 B1 | 5/2001 | Sherman et al. |
| 6,274,092 B1 | 8/2001 | Itoh |
| 6,335,166 B1 | 1/2002 | Ammann et al. |
| 6,618,981 B1 | 9/2003 | Rodriguez |
| 2002/0021983 A1 | 2/2002 | Comte et al. |
| 2002/0108917 A1 | 8/2002 | Maruyama |

FOREIGN PATENT DOCUMENTS

| | | |
|---|---|---|
| EP | 0 965 385 A2 | 12/1999 |
| EP | 0965385 A2 | 12/1999 |

* cited by examiner

SAMPLE CARRIER

This application claims the benefit of U.S. Provisional Application No. 60/307,047, filed Jul. 20, 2001, the contents of which are hereby incorporated by reference herein.

FIELD OF THE INVENTION

The present invention relates to a sample carrier for holding and centering a plurality of sample tubes. The sample carrier of the present invention can be adapted for use with an automated sampling system and is designed for holding sample tubes having penetrable caps. The present invention further relates to a drip shield for protecting against cross-contamination between sample tubes and for substantially limiting vertical movement of sample carriers positioned on conveying means during an automated sample transfer.

INCORPORATION BY REFERENCE

All references referred to herein are hereby incorporated by reference in their entirety. The incorporation of these references, standing alone, should not be construed as an assertion or admission by the inventors that any portion of the contents of all of these references, or any particular reference, is considered to be essential material for satisfying any national or regional statutory disclosure requirement for patent applications. Notwithstanding, the inventors reserve the right to rely upon any of such references, where appropriate, for providing material deemed essential to the claimed invention by an examining authority or court. No reference referred to herein is admitted to be prior art to the claimed invention.

BACKGROUND OF THE INVENTION

Procedures for determining the presence or absence of specific organisms or viruses in a test sample commonly rely upon nucleic acid-based probe testing. To increase the sensitivity of these tests, an amplification step is often included to increase the number of potential nucleic acid target sequences present in the test sample. There are many procedures for amplifying nucleic acids which are well known in the art, including, but not limited to, the polymerase chain reaction (PCR), (see, e.g., Mullis, "Process for Amplifying, Detecting, and/or Cloning Nucleic Acid Sequences," U.S. Pat. No. 4,683,195), transcription-mediated amplification (TMA), (see, e.g., Kacian et al., "Nucleic Acid Sequence Amplification Methods," U.S. Pat. No. 5,399,491), ligase chain reaction (LCR), (see, e.g., Birkenmeyer, "Amplification of Target Nucleic Acids Using Gap Filling Ligase Chain Reaction," U.S. Pat. No. 5,427,930), and strand displacement amplification (SDA), (see, e.g., Walker, "Strand Displacement Amplification," U.S. Pat. No. 5,455,166). A review of several amplification procedures currently in use, including PCR and TMA, is provided in HELEN H. LEE ET AL., NUCLEIC ACID AMPLIFICATION TECHNOLOGIES (1997).

A concern with amplification is the possibility of cross-contamination, since transferring even a minute amount of target-containing sample to a target-negative sample could lead to the production of billions of target sequences in the "negative" sample. As a consequence, a test may indicate a positive result for a sample actually lacking nucleic acid from an organism or virus of interest. The source of a contaminating sample transfer may be an aerosol or bubbles released from a sample tube when a cap component of the sample tube is removed by a practitioner or instrument. To minimize such sources of contamination, penetrable caps having filtering means were recently introduced and are disclosed by Anderson et al., "Collection Device and Method for Removing a Fluid Substance from the Same," U.S. Patent Application No. 20010041336 A1, and Kacian et al., "Penetrable Cap," U.S. application Ser. No. 10/093,511, both of which enjoy common ownership herewith.

To limit the force required to penetrate a sample tube having a penetrable cap, it is important for the penetrable surface of the cap to be centered under a robotic pipettor in an automated sampling system. See, e.g., Ammann et al., "Automated Process for Isolating and Amplifying a Target Nucleic Acid Sequence," U.S. Pat. No. 6,335,166, which enjoys common ownership herewith (an instrument for performing amplification assays on test samples which includes a robotic pipettor for obtaining test sample from a sample tube is disclosed). By centering the penetrable cap, a pipette tip fixed to the robotic pipettor may be programmed to contact and pierce a weak point on the cap. See, e.g., Anderson et al., U.S. patent application Ser. No. 20010041336 A1 (a plastic, conically-shaped, striated cap is disclosed in one embodiment). And, if the filtering means included in the penetrable cap provides the least resistance if it is centered under the cap, as with a material which is rolled or contains a center cut or bore, then the pipette tip will encounter the least resistance with the filter if the pipette tip is centered on the penetrable surface of the cap.

Conventional sample carriers commonly rely upon springs to immobilize distal ends of sample tubes, biasing the sample tubes against one or more opposing surfaces of the sample carriers. While these sample carriers are generally adequate to hold open-ended sample tubes during transport and pipetting in an automated sampling system, they do not include a mechanism for maintaining the sample tubes in fixed vertical orientations or for centering sample tubes having vessel components of varying diameters. As a result, conventional sample carriers are unreliable for holding and centering sample tubes having penetrable caps whose design and construction requires accurate positioning of the sample tubes in order to minimize the forces needed to penetrate the caps with a robotic pipettor.

Thus, a need exists for a sample carrier which maintains sample tubes in fixed vertical orientations, permitting penetrable cap components of the sample tubes to be centered under and pierced by a robotic pipettor within an automated sampling system using minimal force. By centering closed sample tubes for penetration by a robotic pipettor, filters contained within the caps of the sample tubes should be able function optimally as barriers to contaminating aerosols and bubbles present in the sample tubes and to remove sample residue from the outer surfaces of pipette tips as they are being withdrawn from the sample tubes.

SUMMARY OF THE INVENTION

The present invention solves the centering problems associated with conventional sample carriers by providing a sample carrier which comprises a top wall, a base and a support wall joining the top wall and the base. The top wall includes a plurality of spaced-apart openings, where each opening is dimensioned to receive one of a plurality of sample tubes therethrough and to accommodate a cap component fixed to an open end of a vessel component of the sample tube. The base defines a plurality of sample tube holding areas, where each sample tube holding area corresponds to an opening in the top wall and includes one or more retaining walls extending upward from the base. The retaining walls are opposed to the support wall and function to hold a sample tube in a substantially fixed, vertical orientation below the corresponding opening in the top wall. A plurality of springs extend outward from the support wall, where each spring is associated with one of the sample tube holding areas. The springs are configured and arranged so that each spring biases a sample tube against the retaining walls of the associated sample tube holding area during use. The top wall is configured and arranged so that the cap component of each sample tube is positioned within one of the openings when the vessel component is held in the corresponding sample tube holding area. The sample carrier may be of any shape, but is preferably arcuately shaped for use on an automated sample carousel.

In a preferred embodiment, the top wall of the sample carrier extends laterally in both directions from the support wall and includes a series of aligned openings along opposite sides of the support wall. The openings are preferably circular in geometry, and the size of the openings may be the same or different to accommodate sample tubes having caps of equal or different diameters. Preferably, the top wall is chamfered about the periphery of each opening to facilitate insertion of the sample tubes into the sample tube holding areas.

In another embodiment of the present invention, the sample carrier further includes a plurality of sleeves, where each sleeve depends from a bottom surface of the top wall and circumscribes one of the openings. The inner surface of each sleeve is dimensioned to receive a vessel component of a sample tube and accommodates a cap component of the sample tube in touching contact at a proximal end of the sleeve adjacent an inner surface of the opening. Each sleeve is preferably integrally molded with an outer surface of the support wall and with each adjacent sleeve on the same side of the support wall. To permit viewing or scanning of machine readable labels affixed to the sample tubes, each sleeve preferably includes an outwardly facing opening which is configured and arranged to provide a substantially unobstructed view of the label. The label may be a scannable bar code, for example, and can be used for purposes such as patient identification, identifying the sample material, and/or to indicate the type of analysis or analyses to be performed on the sample.

In still another embodiment of the present invention, the top wall has upwardly flared edges to facilitate handling of the sample carrier and to minimize user contact with the sample tubes. In a preferred embodiment, the edges further include a series of recesses. Pairs of opposed recesses are positioned adjacent openings in the top wall to accommodate insertion and removal of sample tubes from and into the sample tube holding areas.

In yet another embodiment of the present invention, the sample tube holding areas are each provided with a pair of opposed retaining walls. A proximal end of each retaining wall preferably slopes inward into the corresponding sample tube holding area to facilitate insertion of sample tubes into the sample tube holding area. The retaining walls are angled with respect to an outer surface of the support wall to accommodate sample tubes of varying diameters. The angle of each retaining wall with respect to the outer surface of the support wall is preferably in the range of 35° to 55°. In addition to being angled, each retaining wall preferably extends from an end wall of the support wall or from a partition extending upward from the base and, in a preferred embodiment, radially or perpendicularly outward from the support wall. In another preferred embodiment, one of the two retaining walls from each of two adjacent sample tube holding areas extends from the partition separating the adjacent sample tube holding areas, thereby forming a Y-shaped divider.

In a further embodiment of the present invention, each spring is a leaf spring which includes one or a pair of spring arms extending outward and downward from one or both sides of the outer surface of the support wall and are configured and arranged so that sample tubes are biased against the retaining walls in respective sample tube holding areas. Surfaces of the spring arms can be chemically or physically altered to increase the coefficient of friction between the spring arms and outer surfaces of the sample tubes. Regardless of the types of springs used, the springs preferably have a holding force of at least about 1.0 pound force (4.45 N) and more preferably of at least about 1.5 pounds force (6.67 N). As used herein, the phrase "holding force" refers to the force a spring exerts against a sample tube in a sample tube holding area, and the term "spring" is to be given its ordinary meaning, referring to an elastic device which regains its original shape after being compressed.

In still another embodiment of the present invention, the inner surfaces of the openings and sleeves are dimensioned so that penetrable cap components of the sample tubes are centered within the openings when the sample tubes are inserted into the sample tube holding areas. Centering of the caps prior to piercing with a robotic pipettor can help to limit the forces required to pierce the caps and can provide for more accurate pipetting. In a preferred embodiment, the sample tubes are centered for cap piercing to within about 0.125 inches (3.18 mm) from the longitudinal axis of a top surface of the cap component of the sample tube and more preferably to within about 0.1 inches (2.54 mm).

In yet another embodiment of the present invention, the outer surface of the support wall includes a plurality of machine readable labels, each label being affixed to an area of the outer surface of the support wall above a sample tube holding area and below the bottom surface of the top wall. If the sample carrier includes the above-described sleeves, each machine readable label is positioned above a sample tube holding area and below a bottom surface of the corresponding sleeve. These labels may include a scannable bar code or other machine readable information which can be used to indicate whether a sample tube is present in or absent from a particular sample tube holding area.

In a further embodiment of the present invention, a drip shield is provided which protects the contents of sample tubes held by a sample carrier from fluid contamination, especially hanging droplets which may be dislodged from a robotic pipettor during an automated sampling procedure. The drip shield includes a cover plate which may have an arcuate shape conforming to the arcuate shape of the preferred sample carriers.

The cover plate of the drip shield includes one or more through-holes, where each through-hole is configured and arranged to provide non-interfering, vertical passage of an aligned pipette tip therethrough. The through-holes are sized to permit access to the contents of only one sample tube at a time, where the sample tubes being accessed are present in a sample carrier positioned beneath the cover plate. In a preferred embodiment, the diameter of each through-hole is the same as or smaller than the greatest diameter of any sample tube carried by the sample carrier to minimize opportunities for contaminating the sample carrier and its contents. A top surface of the cover plate may be chamfered or, alternatively, include a rim about the periphery of each through-hole. A chamfered through-hole could aid in redirecting a misaligned pipette tip through the through-hole, whereas a rimmed through-hole would provide a further barrier to fluid contamination of sample tubes. Where the sample carrier includes two sets of openings on opposite sides of the support wall, the preferred drip shield includes two through-holes, where the two through-holes in the cover plate are configured to provide access to sample tubes on opposite sides of the support wall.

Depending from a bottom surface of the cover plate is a fin or series of aligned fins, where the fin or fins are configured and arranged to limit vertical movement of a sample carrier positioned beneath the drip shield. If the sample carrier includes the preferred two sets of openings on opposite sides of the support wall, then the fin or fins are substantially longitudinally or arcuately centered on the bottom surface of the cover plate. In this way, the fin or fins are positioned over the support wall rather than over any of the openings in the top wall which are intended to be accessed by a robotic pipettor. The ends of the fin or fins may be tapered so that a sample carrier which is not fully seated in a sample carrier receiving well of a sample carousel may be progressively forced down into rather than knocked out of the sample carrier receiving well.

In another embodiment of the present invention, an automated sampling system is provided which includes one or more of the above-described sample carriers having a series of aligned openings along opposite sides of the support wall in combination with a sample carrier conveying means and a drip shield which is located above and in fixed relationship to the sample carriers being transported thereunder. By "automated sampling system" is meant a system for holding a sample tube in a substantially vertical orientation and conveying the sample tube by automated means to a location within an apparatus so that sample present in the sample tube may be accessed by a robotic pipettor in order to effect a transfer of at least a portion of the sample to another location within the apparatus.

The drip shield is preferably constructed of a substantially non-conductive material and includes one or more through-holes (preferably two) for accessing the contents of one or more of the sample tubes with at least one robotic pipettor. Sample tubes may accessed independently or simultaneously, depending in part on the number of pipettors used and/or on the number and arrangement of pipettor channels on each pipettor. The drip shield also includes a depending fin which is positioned to separate sample tubes on opposite sides of the support wall and to substantially limit vertical movement of the sample carriers when pipette tips are withdrawn from sample tubes. The fin is preferably positioned so that the drip shield and the sample carriers are not in touching contact before sample is removed from the sample tubes. The distance between a bottom surface of the fin of the drip shield and top surfaces of the top walls of sample carriers conveyed thereunder is preferably no more than about 0.125 inches. Additionally, to minimize the chance of carry-over contamination, the diameter of each through-hole in the drip shield is preferably about the same as or less than the greatest diameter of any sample tube (especially a cap component) carried by any of the sample carriers. And, consistent with the preferred shape of the sample carrier, the drip shield and its depending fin preferably have a corresponding arcuate shape.

These and other features, aspects, and advantages of the present invention will become apparent to those skilled in the art after considering the following detailed description, appended claims and accompanying drawings.

Figure 1:
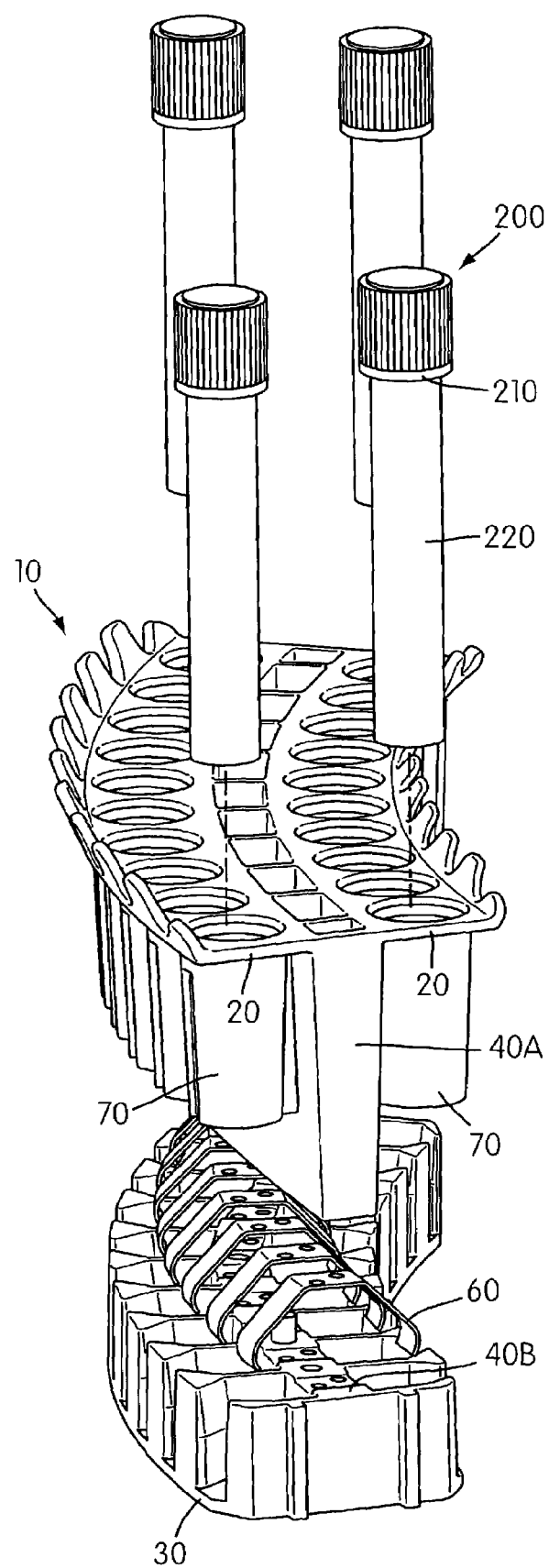
FIG. 1 is an exploded perspective view of a sample carrier according to the present invention and four sample tubes used therewith.

The sample carrier illustrated in the attached drawings includes a number of redundant features. Where it would be clear to those skilled in the art from reviewing the drawings and reading the following description what features are being shown, the inventors have attempted to avoid including an excessive number of reference numbers by providing reference numbers for only a representative number of similar features depicted therein.

DETAILED DESCRIPTION OF THE INVENTION

While the present invention may be embodied in a variety of forms, the following description and accompanying drawings are merely intended to disclose some of those forms as specific examples of the present invention. Accordingly, the present invention is not intended to be limited to the forms or embodiments so described and illustrated. Instead, the full scope of the present invention is set forth in the appended claims.

With reference to the figures, a preferred sample carrier 10 of the present invention is shown alone or in combination with a drip shield 100 for protecting against cross-contamination between sample tubes 200 carried by the sample carrier and for limiting vertical movement of the sample carrier when sample is being removed from any of the sample tubes. Sample carriers 10 of the present invention are preferably used in combination with sample tubes 200 having sealed caps 210 which can be penetrated by standard pipette tips for use with positive displacement pipettes. To ensure proper alignment for penetrating these caps 210 and pipetting sample, the sample carriers 10 of the present invention substantially immobilize the sample tubes 200 they carry, thereby limiting both vertical and lateral movement of the sample tubes during sampling procedures. The sample tubes 200 used with the sample carriers 10 of the present invention may be transport tubes provided with sample collection kits which are used to receive and store samples for shipping and future analysis, including analysis with nucleic acid-based assays or immunoassays diagnostic for a particular pathogenic organism or virus. Such samples may include, for example, blood, urine, saliva, sputum, mucous or other bodily secretion, pus, amniotic fluid, cerebrospinal fluid, seminal fluid, tissue specimens, stool, environmental samples, food products, chemicals, powders, particles or granules. The sample tubes 200 may be of any shape or composition, provided a vessel component 220 of the sample tubes is shaped to receive and retain the material of interest (e.g., animal, environmental, industrial, food or water samples). The vessel component 220 includes a closed end and an open end adapted for fixing the cap 210 thereto. Preferred sample tubes are disclosed by Anderson et al., U.S. Patent Application No. 20010041336 A1, and Kacian et al., U.S. application Ser. No. 10/093,511. It is generally important that the composition of the sample tube 200 be essentially inert relative to the sample so that it does not significantly interfere with the performance or results of an assay.

As illustrated in the figures, sample carriers 10 according to the present invention include a top wall 20, a base 30, a support wall 40 which joins the top wall and the base in fixed relationship, and a plurality of springs 60 extending outward from the support wall. The support wall 40 may be an integral component or it may comprise, for example, an upper portion 40A and a lower portion 40B, as shown in FIG. 1. In a preferred embodiment, the top wall 20 and the upper portion 40A of the support wall 40 form one integral component and the base 30 and the lower portion 40B of the support wall form another integral component, the two components being joined together by such means as a snap-fit, ultrasonic welding, adhesive, screws, clips or other mechanical fasteners.

Figure 2:
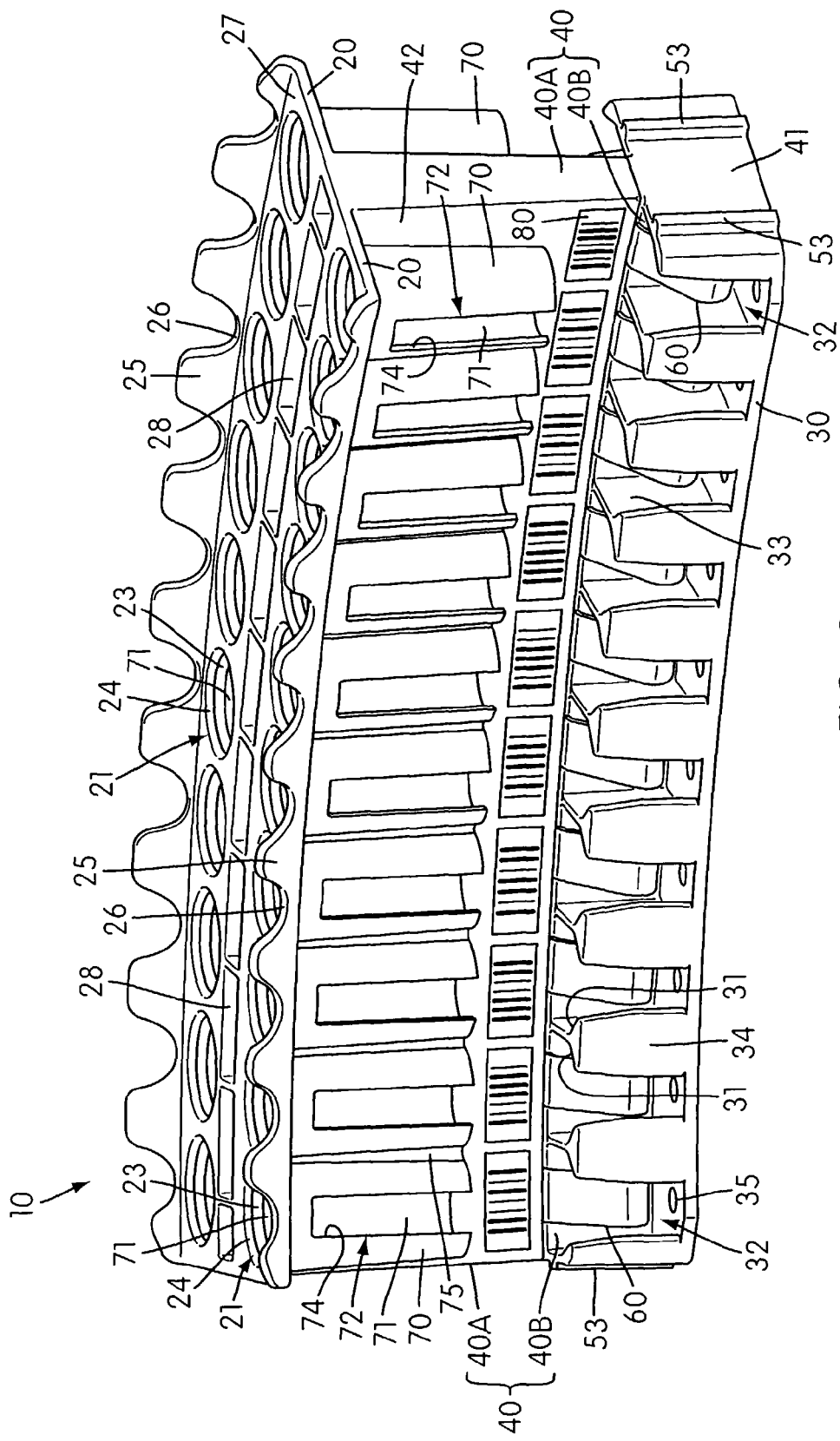
FIG. 2 is a front perspective view of the sample carrier of FIG. 1.
Figure 3:
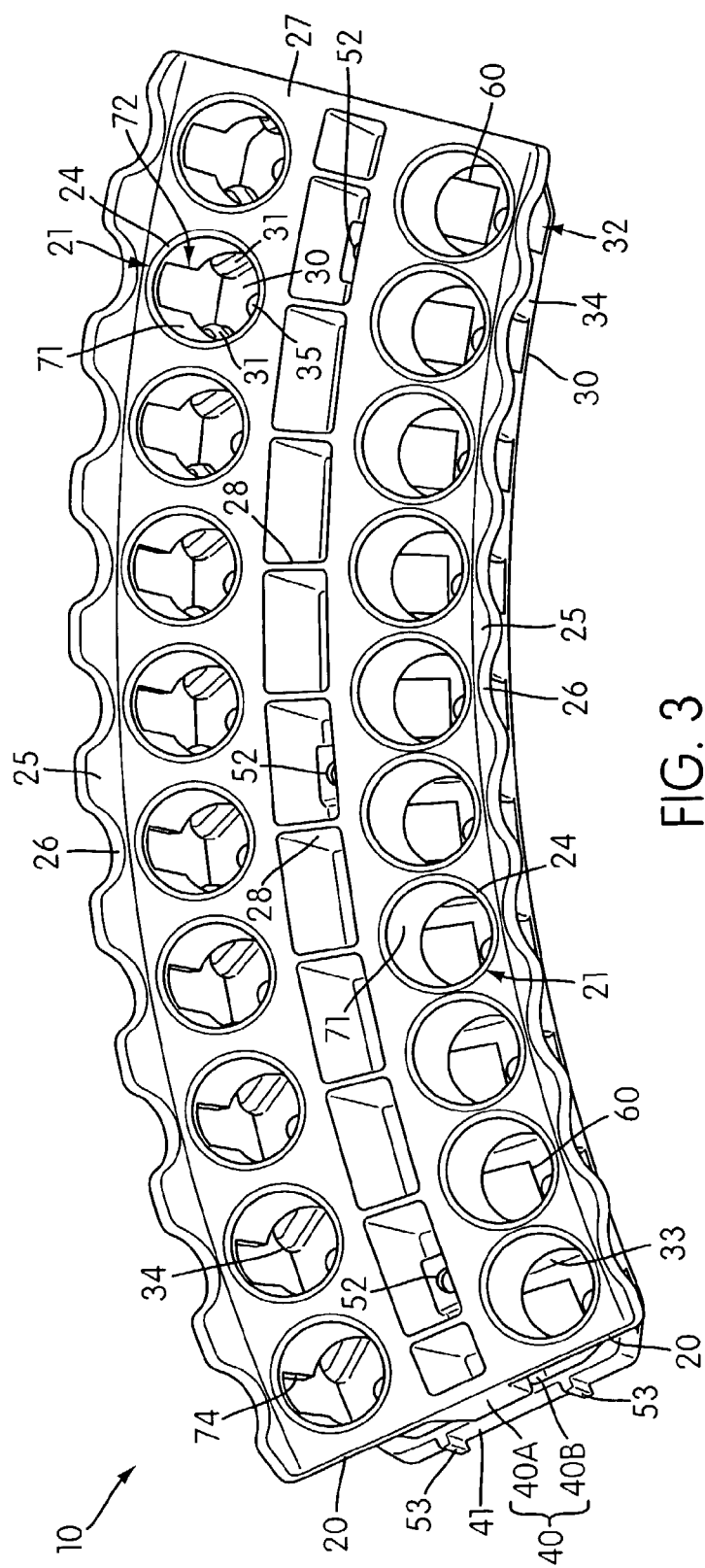
FIG. 3 is a top plan view of the sample carrier of FIG. 1.
Figure 7:
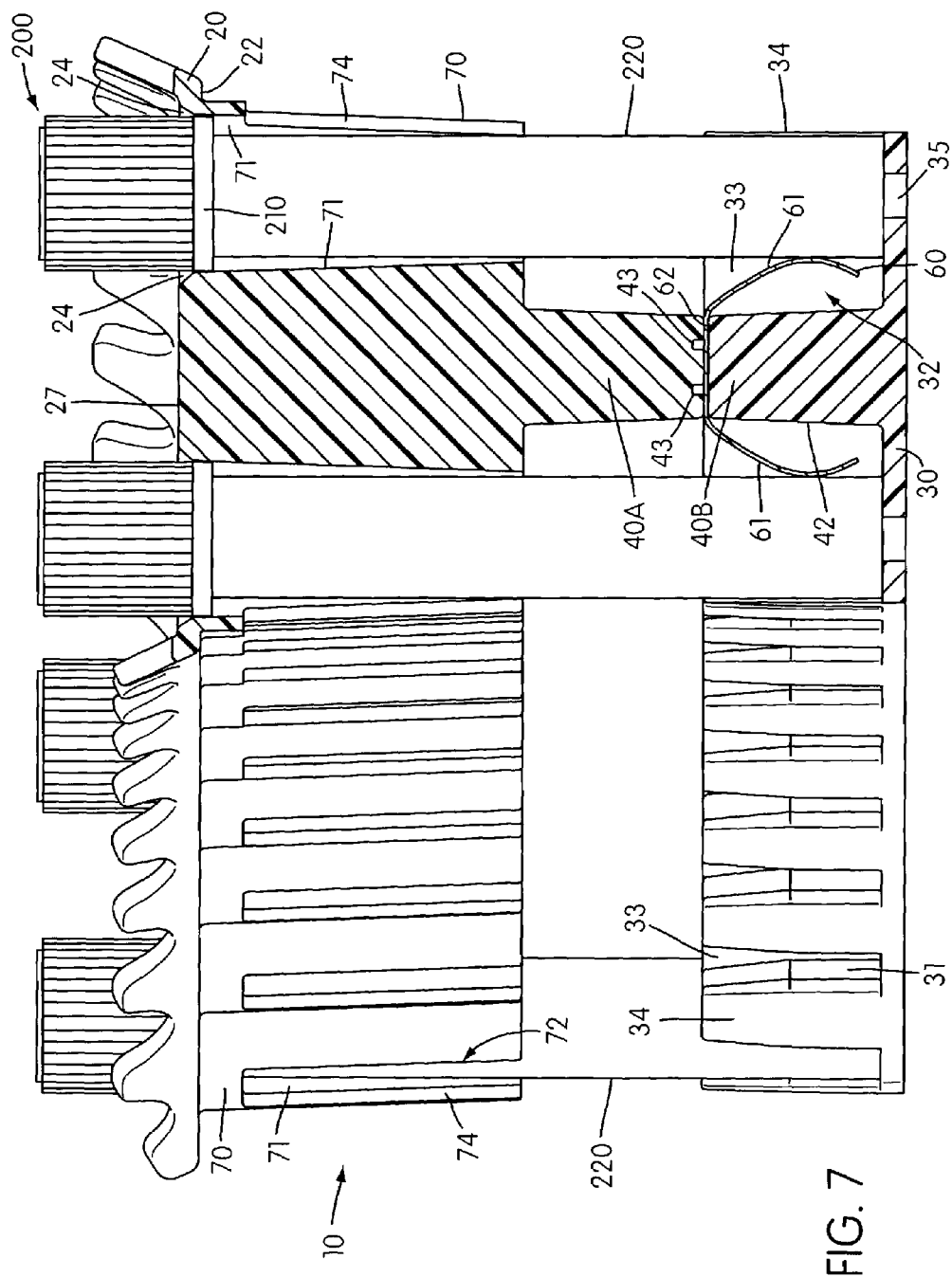
FIG. 7 is an enlarged section end view of the sample carrier of FIG. 6, taken along the 7—7 line thereof.

Spaced-apart openings 21 are included in the top wall 20 (see FIGS. 2 and 3) which may be of the same or different sizes and are dimensioned to receive sample tubes 200 into the sample carrier 10. As illustrated in FIGS. 2, 3 and 7, the top wall 20 includes a chamfered ring 24 circumscribing each opening 21 to facilitate insertion of the sample tubes 200 into the sample carrier 10. The figures show a preferred embodiment in which the top wall 20 extends laterally in both directions relative to the support wall 40 and includes a series of openings 21 aligned along each side of the support wall. The number of openings 21 on each side of the support wall 40 is preferably 10. The present invention also contemplates sample carriers (not shown) which include a single series of openings 21 in the top wall 20, where the top wall extends laterally in only one direction relative to the support wall 40.

Figure 6:
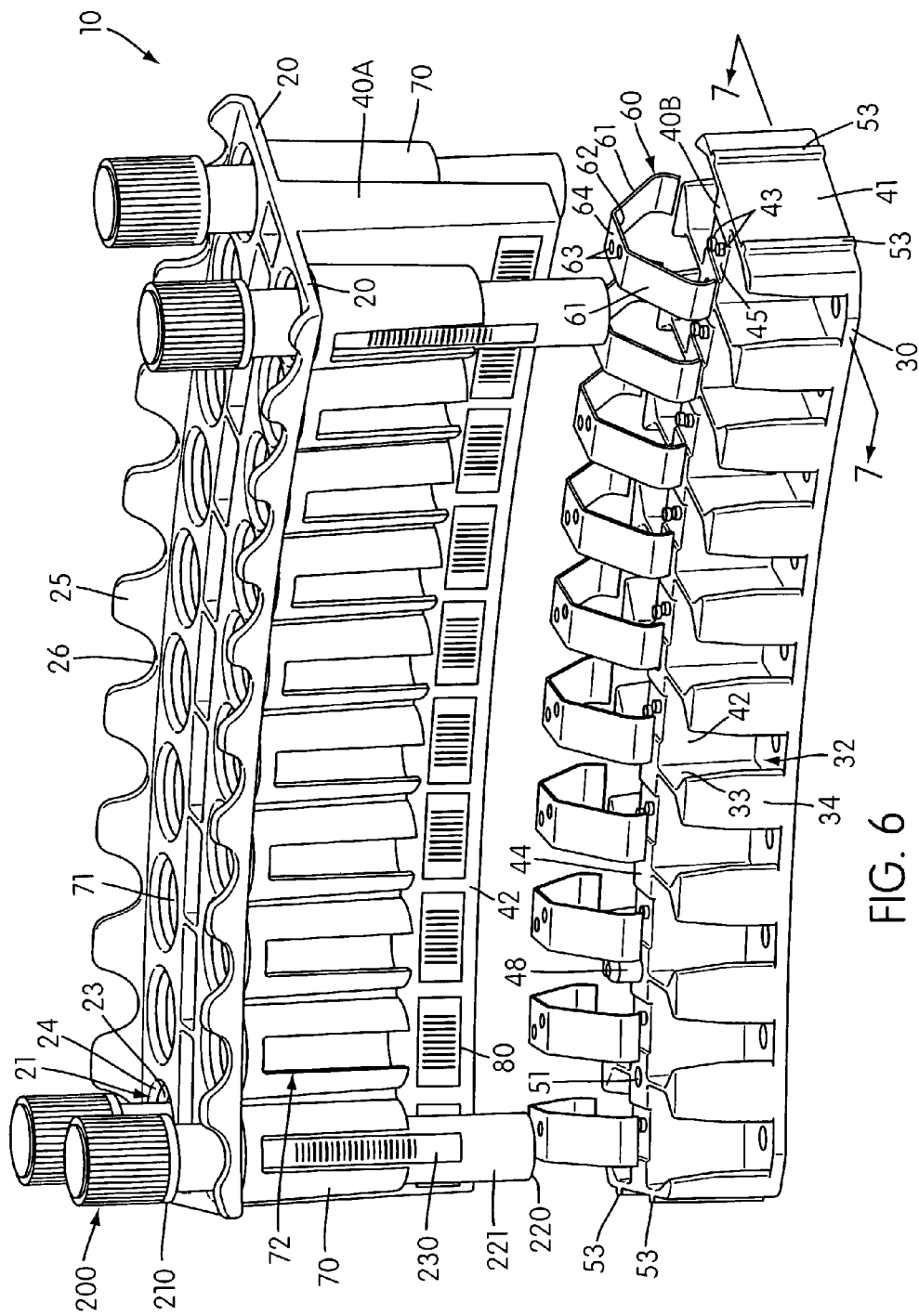
FIG. 6 is an exploded, perspective front view of the sample carrier of FIG. 1 and the four sample tubes used therewith.

The springs 60 may extend directly from the support wall 40 or, as shown in FIGS. 1 and 6, from between the upper and lower portions 40A, 40B of the support wall. The springs 60 function to bias sample tubes 200 against retaining walls 31 which are opposed to the support wall 40 and extend upward from the base 30.

In a preferred embodiment shown in FIG. 2, a sleeve 70 is included which depends from a bottom surface 22 of the top wall 20 and circumscribes each opening 21. While not necessary for immobilizing sample tubes 200 in the sample carrier 10, the sleeves 70 can aid in guiding the distal portions of sample tubes into sample tube holding areas 32 located at the base 30 of the sample carrier. The base 30 defines a plurality of sample tube holding areas 32, each sample tube holding area constituting the space on and above the base between the support wall 40 and a corresponding pair of retaining walls 31. End walls 41 and a plurality of partitions 33 extending upward from the base 30 and radially or perpendicularly outward from to the lower portion 40B of the support wall 40 may be further included, as shown in FIG. 6, which further define the boundaries of the sample tube holding areas 32. When included, the partitions 33 need not extend directly from the support wall 40.

The illustrated sleeves 70 are tapered, each having an annular, inner surface 71 which is preferably coincident with an annular, inner surface 23 of the corresponding opening 21 (see, e.g., FIG. 7). The inner surfaces 71, 23 of the sleeves 70 and openings 21 are sized to receive a cap component 210 of the sample tubes 200 in touching contact, which may be a frictional fit, preferably allowing the longitudinal axis of the cap component 210 to move laterally from the longitudinal axis of the opening 21 no more than about 0.125 inches (3.12 mm), and more preferably no more than about 0.1 inches (2.54 mm). To permit viewing or scanning of a human or machine readable label 230 (e.g., scannable bar code) which may be affixed to an outer surface 221 of the sample tube 200, each sleeve 70 includes an outwardly facing, elongate opening 72 which extends upward from a bottom surface 73 of the sleeve and terminates at a surface 74 below or substantially coincident with the bottom surface 22 of the top wall 20. For stability, FIGS. 2 and 8 illustrate that sample carriers 10 of the present invention can be molded to include a first bridge 75 which connects adjacent sleeves 70 and a second bridge 76 which connects each sleeve to the support wall 40.

Figure 9:
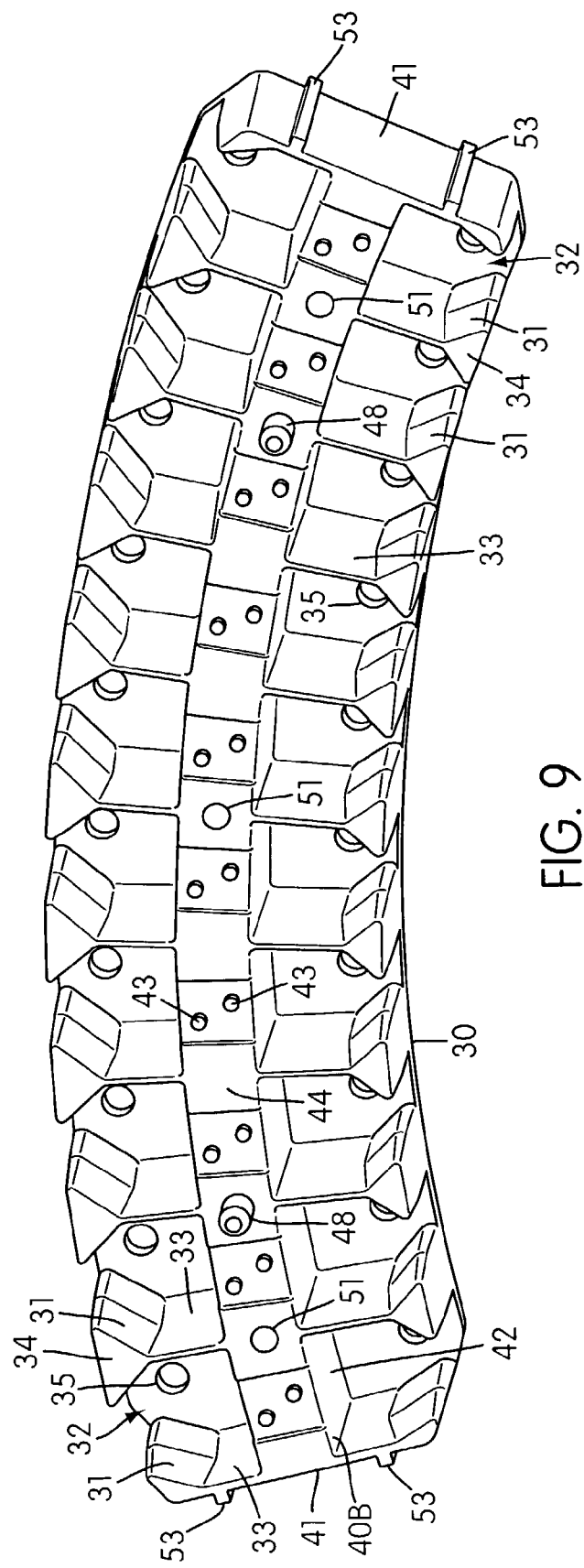
FIG. 9 is a perspective top view of the lower portion of the support wall of FIG. 6.

As described above, the sample tube holding areas 32 are defined by base 30 regions located directly below the openings 21 in the top wall 20 and are configured to hold sample tubes 200 in substantially vertical orientations in the sample carrier 10, as shown in FIG. 7. In the preferred embodiment shown in FIG. 9, the sample tube holding areas 32 include a pair of opposed retaining walls 31, each having an angled orientation relative to the support wall 40. In this preferred embodiment, the angle of each retaining wall 31 relative to the support wall 40 is preferably between 35° and 55°, more preferably between 40° and 50°, and most preferably about 45°. To facilitate insertion of sample tubes 200 into corresponding sample tube holding areas 32, proximal ends of the retaining walls 31 preferably slope inward into the corresponding sample tube holding areas. Each retaining wall 31 preferably extends from one of the partitions 33 or one of the end walls 41 of the support wall 40. As depicted in FIG. 9, each partition 33 and a pair of extending retaining walls 31 preferably form a solid "Y" shaped divider 34. A hole 35 is centered in the base 30 of each sample tube holding area 32 for draining corrosive agents, such as bleach, from the sample carrier 10.

Referring to the figures generally, the springs 60 discussed above extend from the support wall 40 into the sample tube holding areas 32. The preferred springs 60 of the present invention are leaf springs made of stainless steel and include at least one spring arm 61 which extends outward and downward from the support wall 40, providing a sufficient degree of tension to their respective sample tubes 200 to hold the sample tubes in an immobilized state as aliquots of sample are being removed from the sample tubes. The holding force of each spring 60 is preferably at least about 1.0 pound force (4.45 N), and more preferably at least about 1.5 pounds force (6.67 N). To increase the coefficient of friction between the springs 60 and outer surfaces 221 of the vessel components 220 of the sample tubes 200, the spring arms 61 may be physically or chemically altered, such as by sand-blasting or etching the surface of the spring arms using techniques well known in the art. The coefficient of friction should not be so great that the sample tubes 200 cannot be manually removed from the sample tube holding areas 32 without difficulty. FIG. 7 provides an enlarged, section side view of the sample carrier 10 showing two sample tubes 200 which have been secured in the sample tube holding areas 32 by the leaf springs 60.

Figure 8:
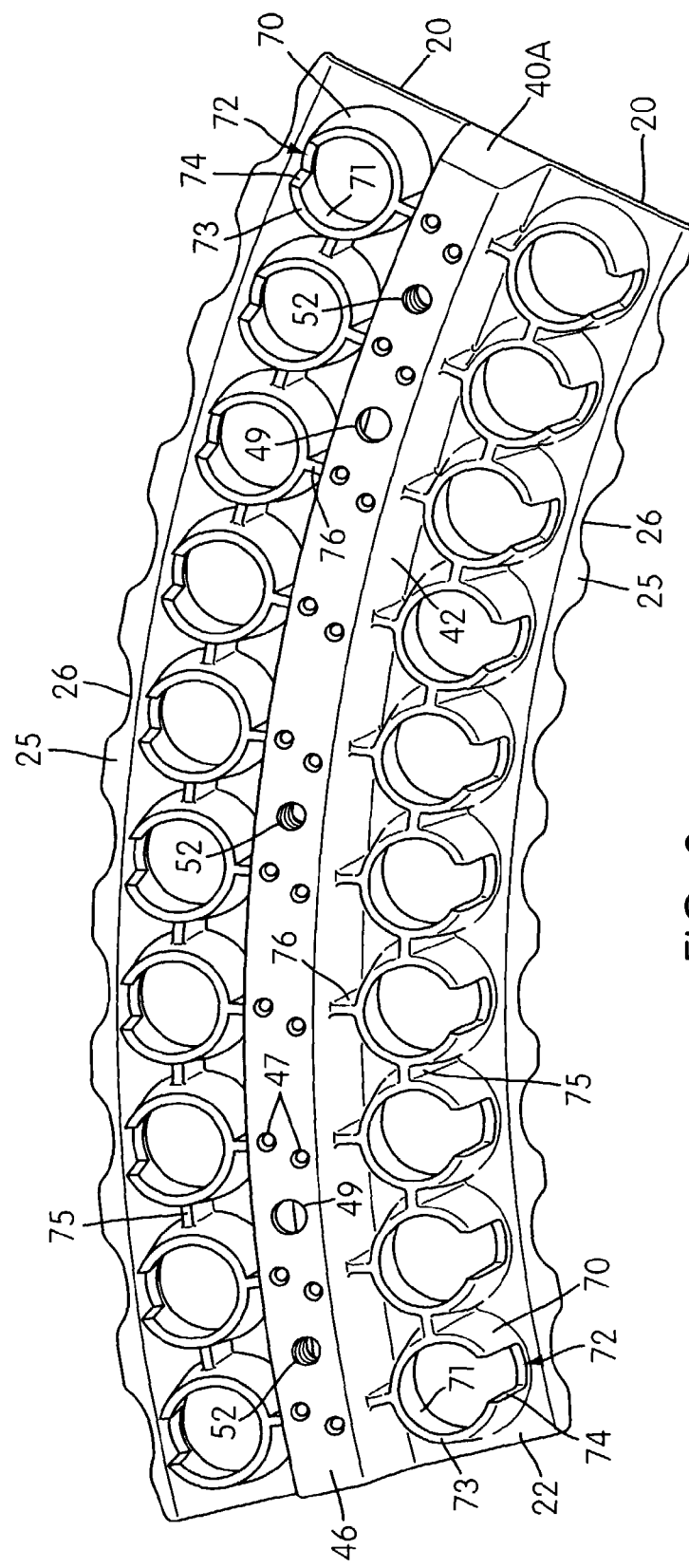
FIG. 8 is a perspective bottom view of the upper portion of the support wall of FIG. 6.

FIGS. 6, 8 and 9 illustrate the preferred means for attaching the springs 60 to the support wall 40. As shown, a joining section 62 of each spring 60 connects pairs of spring arms 61 and is provided with two diagonally positioned through-holes 63 mated with a pair of diagonally positioned bosses 43 located on a top surface 44 of the lower portion 40B of the support wall 40 above each sample tube holding area 32. The bosses 43 extend above the top surface 44 of the lower portion 40B of the support wall 40. So that a top surface 64 of each joining section 62 is flush with adjacent regions of the top surface 44 of the lower portion 40B of the support wall 40, the top surface includes recessed areas 45 dimensioned to receive the joining sections.

Figure 4:
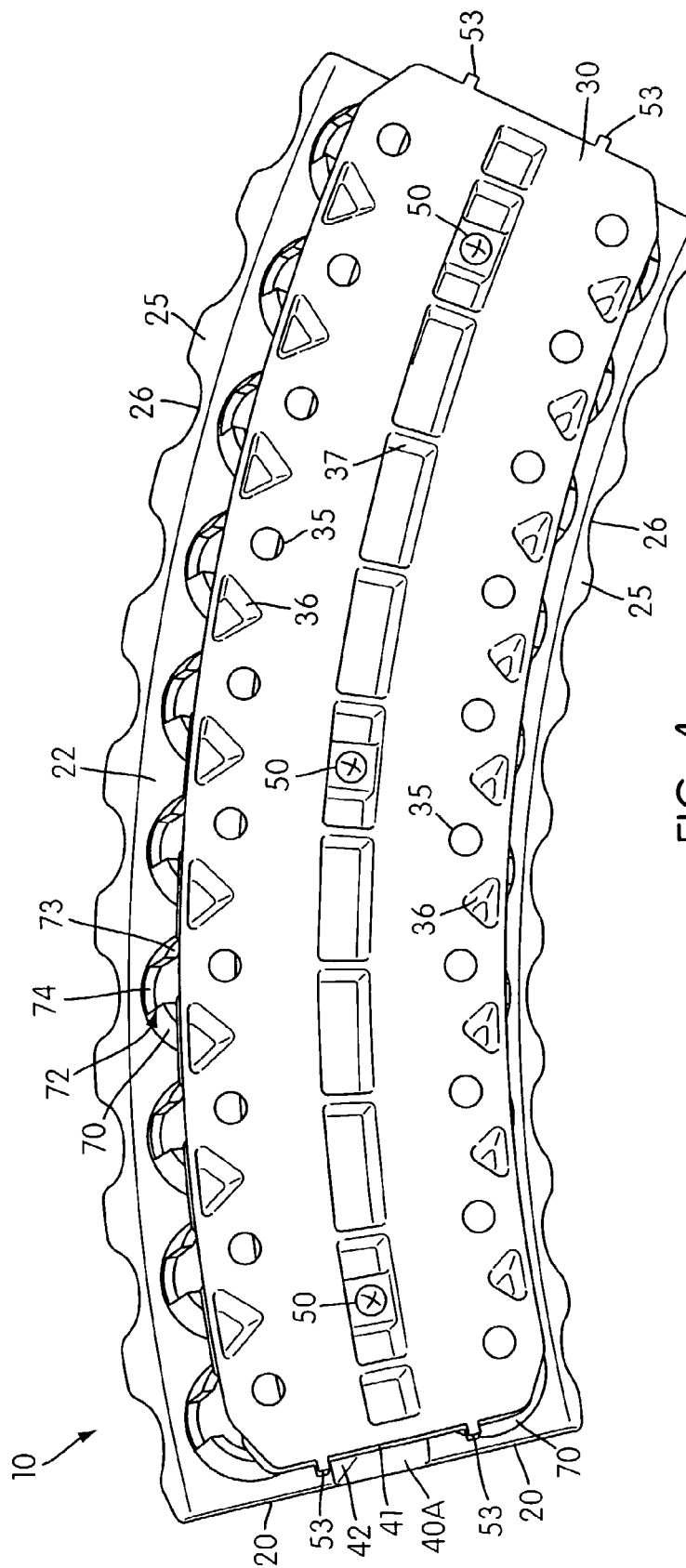
FIG. 4 is a bottom view of the sample carrier of FIG. 1.

Once the springs 60 have been positioned in the recessed areas 45, the upper portion 40A of the support wall 40 can be fitted onto the lower portion 40B of the support wall 40B and securely attached thereto by such means as a snap-fit, clips, screws or other mechanical fasteners. To secure the joining sections 62 in the recessed areas 45, a bottom surface 46 of the upper portion 40A of the support wall 40 is provided with pairs of diagonally positioned cavities 47 mated with the bosses 43 positioned on the top surface 44 of the lower portion 40B of the support wall. Two spaced-apart protuberances 48 on the top surface 44 of the lower portion 40B of the support wall 40 and two corresponding through-holes 49 on the bottom surface 46 of the upper portion 40A of the support wall are provided to properly register the upper and lower portions of the support wall. As illustrated in FIGS. 4, 8 and 9, three screws 50 extending through spaced-apart through-holes 51 in the lower portion 40B of the support wall 40, and screwed into three mated brass threads 52 located on and recessed from a bottom surface 46 of the upper portion 40A of the support wall, is the preferred means for securing the lower and upper portions of the support wall to each other.

Figure 5:
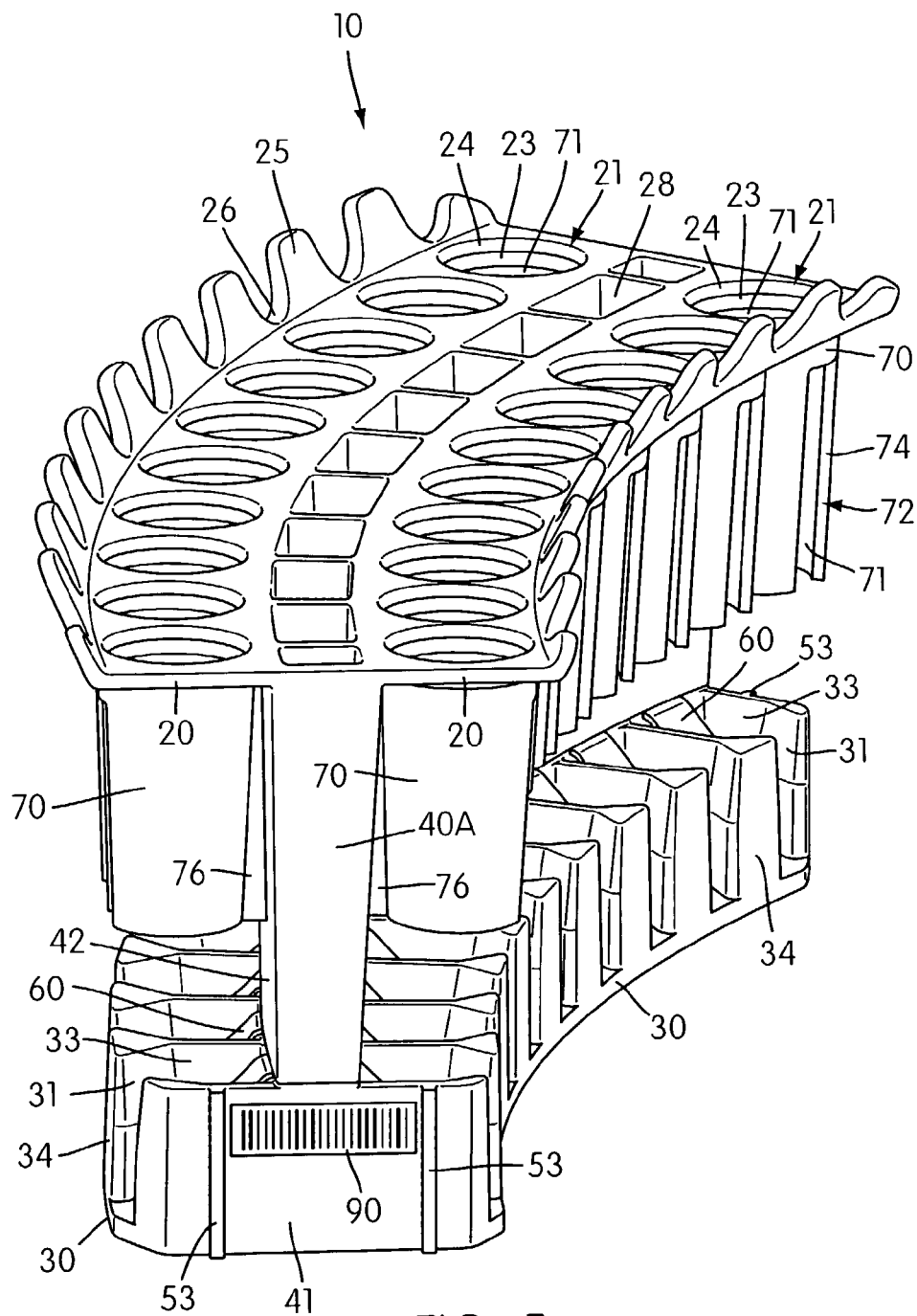
FIG. 5 is a perspective end view of the sample carrier of FIG. 1.

To minimize handling of the sample tubes 200, edges 25 of the top wall 20 extend upward, and are preferably flared upward, as shown in FIG. 5. Besides providing a means for limiting contact with the sample tubes 200, the edges 25 can also facilitate gripping and handling of the sample carrier 10. The edges 25 may be modified to include recesses 26, preferably the generally U-shaped recesses shown in FIG. 2, which give the edges a scalloped appearance. If included, the recesses 26 are sized and arranged to permit finger access to sample tubes 200 present in the sample carrier 10.

For automated applications, it is desirable to include means for determining whether a sample tube 200 is present in or absent from a particular sample tube holding area 32 prior to pipetting. This can be achieved in the present invention by providing a machine readable label 80 to an outer surface 42 of the support wall 40 above the lower portion 40B of the support wall, or above each spring 60 if the support wall is integrally molded, and below the bottom surface 73 of each sleeve 70, as indicated in FIG. 2. If a sample tube 200 inserted into a sample tube holding area 32 is sufficiently translucent, a machine for reading the labels 80 (e.g., bar code scanner) will be unable to read or detect the label behind the sample tube 200. Based its failure to read the label 80 behind the sample tube 200, the reading machine can communicate to a computer controlling the operation of an associated automated sampling system, (see, e.g., FIG. 10), that a sample tube 200 is present in that particular sample tube holding area 32. As a result, a robotic pipettor (not shown) associated with the automated sampling system will be instructed draw a predetermined amount of sample from the sample tube at that location. But, if a sample tube 200 is absent from a sample tube holding area 32, a reading machine associated with the automated sampling system will be able to read or detect the corresponding label 80 and will communicate to the computer that a sample tube 200 is missing from that sample tube holding area. Accordingly, no instruction will be given to the robotic pipettor to draw sample from that location.

Figure 10:
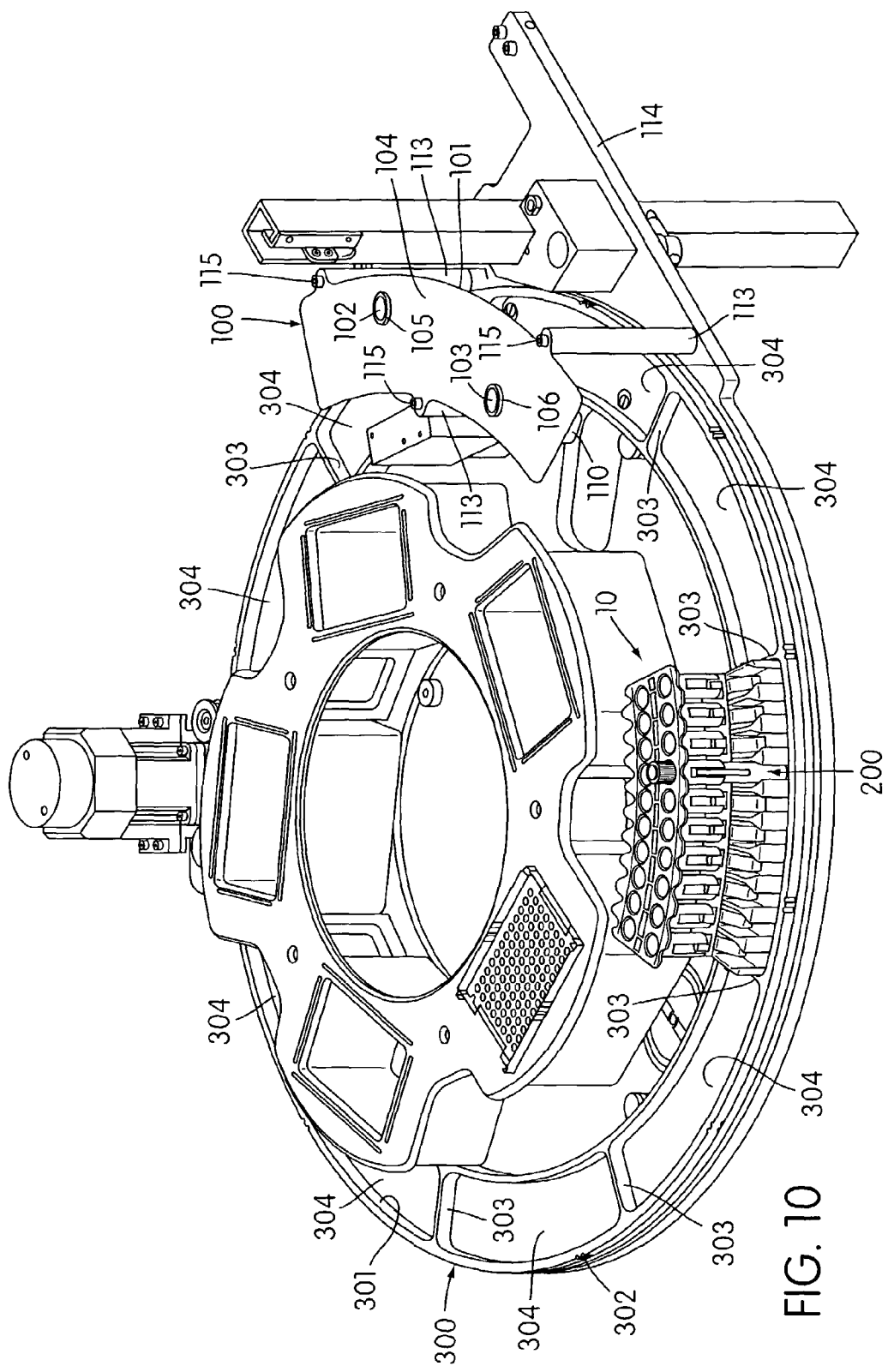
FIG. 10 shows the sample carrier of FIG. 1 positioned on a sample carousel and holding a single sample tube.

The base 30 of the sample carrier 10 may be adapted for use with a sample carrier conveying means, such as a sample carousel for rotating a plurality of sample carriers within an automated sampling system. One such sample carousel 300 is disclosed by Ammann et al. in U.S. Pat. No. 6,335,166 and is illustrated in FIG. 10. This particular sample carousel 300 is formed of milled, unhardened aluminum and includes an annular trough 301 about the periphery of a ring 302 and a plurality of raised, radially extending dividers 303. The dividers 303 divide the trough 301 into nine arcuate sample carrier receiving wells 304 which can be configured to accommodate the sample carriers 10 of the present invention. The individual sample carrier receiving wells 304 need to be dimensioned to maintain the sample carriers 10 in an upright position as sample tubes 300 held by the sample carriers 10 are indexed under a robotic pipettor (not shown) for retrieving sample material for analysis. As shown in FIG. 5, the sample carriers 10 can be frictionally fitted into the sample carrier receiving wells 304 by providing a pair of vertically extending ribs 53 to each of the end walls 41 of the support wall 40 (see FIG. 6). To track individual sample carriers 10 on the sample carousel 300, a machine readable label 90 (e.g., scannable bar code), can be provided to at least one end wall 41 of the support wall 40, as illustrated in FIG. 5.

Figure 11:
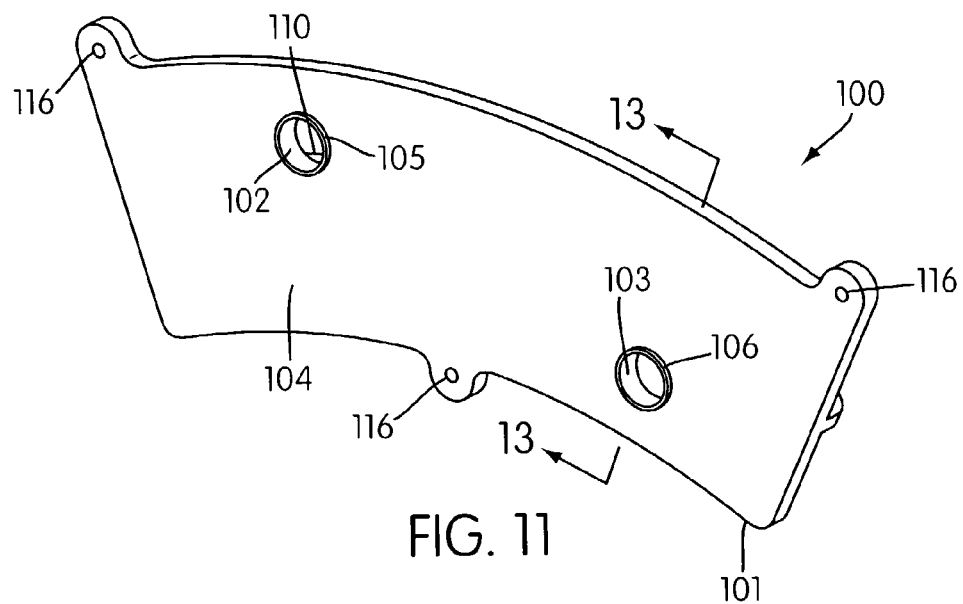
FIG. 11 is a perspective top view of a drip shield according to the present invention.
Figure 13:
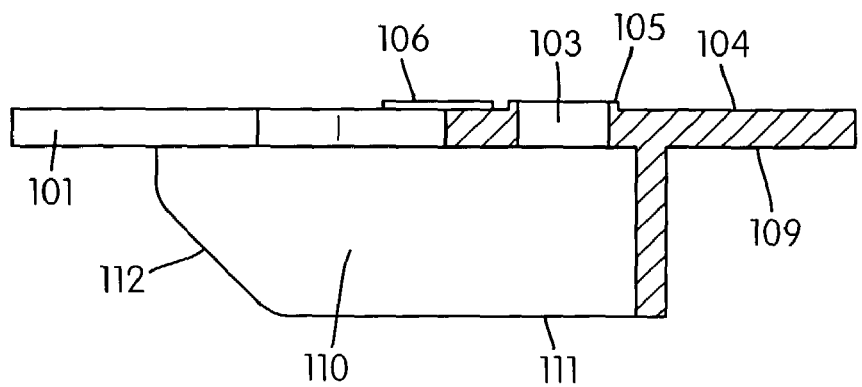
FIG. 13 is a section end view of the drip shield of FIG. 11, taken along the 13—13 line thereof.
Figure 14:
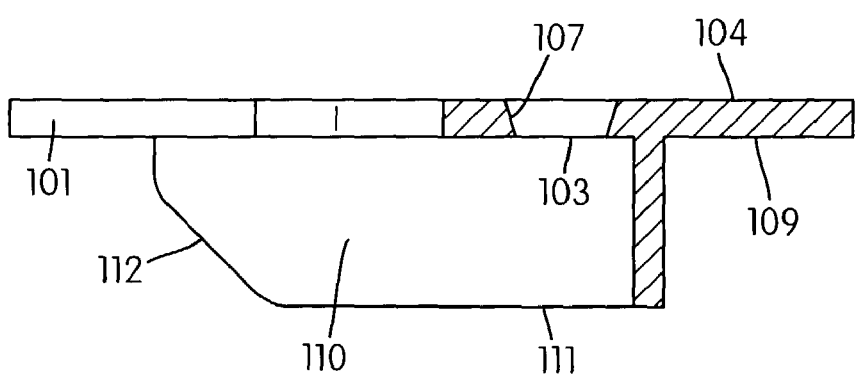
FIG. 14 is a section end view of an alternative drip shield according to the present invention.

The sample carriers 10 of the present invention can be used in combination with a device for protecting sample tubes 200 during sampling to further limit opportunities for cross-contamination. Such a device is provided by a novel drip shield 100 depicted in FIGS. 10–15. This drip shield 100 includes a cover plate 101 which is dimensioned to cover the top surface 27 of the top wall 20. Thus, in a preferred embodiment, the drip shield 100 has an arcuate shape corresponding to the preferred arcuate shape of the sample carrier 10, as shown in FIG. 10. A minimum of two through-holes, identified in FIGS. 10–12 as a first through-hole 102 and a second through-hole 103, extend through the drip shield 100 and provide access to sample tubes 200 centered below the through-holes. The through-holes 102, 103 are dimensioned to permit non-interfering passage therethrough by pipette tips carried by a robotic pipettor, but are small enough so that a top surface 104 of the drip shield 100 can function to catch hanging droplets which are dislodged from the pipette tips during sample transfer procedures. Therefore, the diameters of the first and second through-holes 102, 103, respectively, are preferably about the same as or less than the greatest diameter of any cap component 210 of a sample tube 200 to be carried by a sample carrier 10. Raised annular rims 105, 106 can be provided about the periphery of the first and second through-holes 102, 103, respectively, to impede fluid collected on the top surface 104 of the cover plate 101 from spilling into any of the sample tubes 300, as shown in FIGS. 11 and 13. In a preferred embodiment illustrated in FIG. 14, however, the top surface 104 of the cover plate 101 includes a chamfered ring 107 about the periphery to the first and second through-holes 102, 103, respectively, to aid in redirecting misaligned pipette tips.

The through-holes 102, 103 are arranged on the drip shield 100 so that the first through-hole 102 is positioned above a first or inner row of longitudinally or arcuately aligned sample tubes 200 and the second through-hole 103 is aligned above a second or outer row of longitudinally or arcuately aligned sample tubes. As the sample carrier 10 is indexed forward under the drip shield 100 by the sample carousel 300, the next sample tube 200 in each row of tubes can be presented under one of the through-holes 102, 103 for access by a robotic pipettor. An example of a robotic pipettor for use with the present invention is the Robotic Sample Processor, Model No. RSP9000, available from Cavro, Inc. of Sunnyvale, Calif. The through-holes 102, 103 are preferably offset on the drip shield 100 to further minimize opportunities for contamination resulting from released hanging droplets of sample. In a preferred mode, the through-holes 102, 103 are arranged on the drip shield 100, as shown in FIG. 10, so that the third sample tube 200 in the second or outer row of aligned tubes is being sampled as the first sample tube in the first or inner row of aligned tubes is being sampled.

Figure 12:
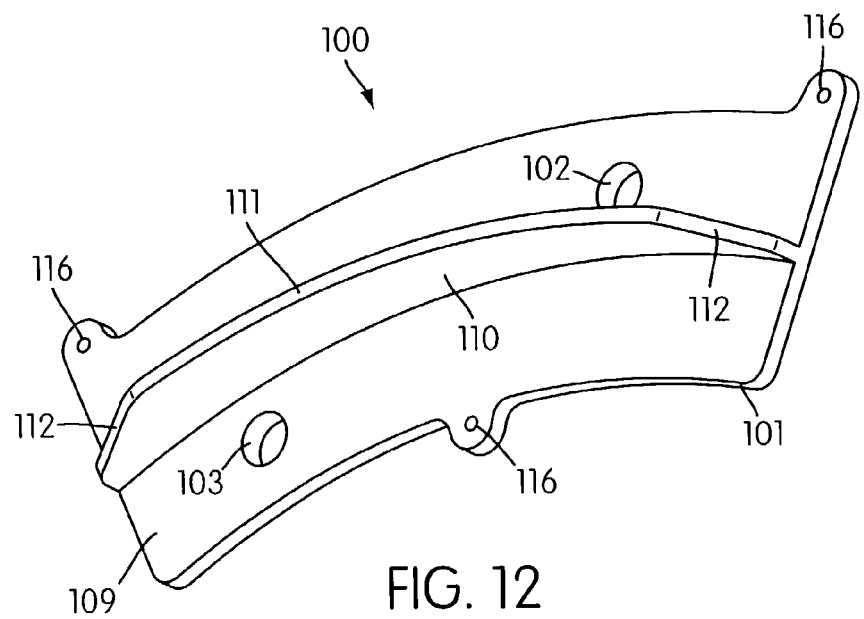
FIG. 12 is a perspective bottom view of the drip shield of FIG. 11.
Figure 15:
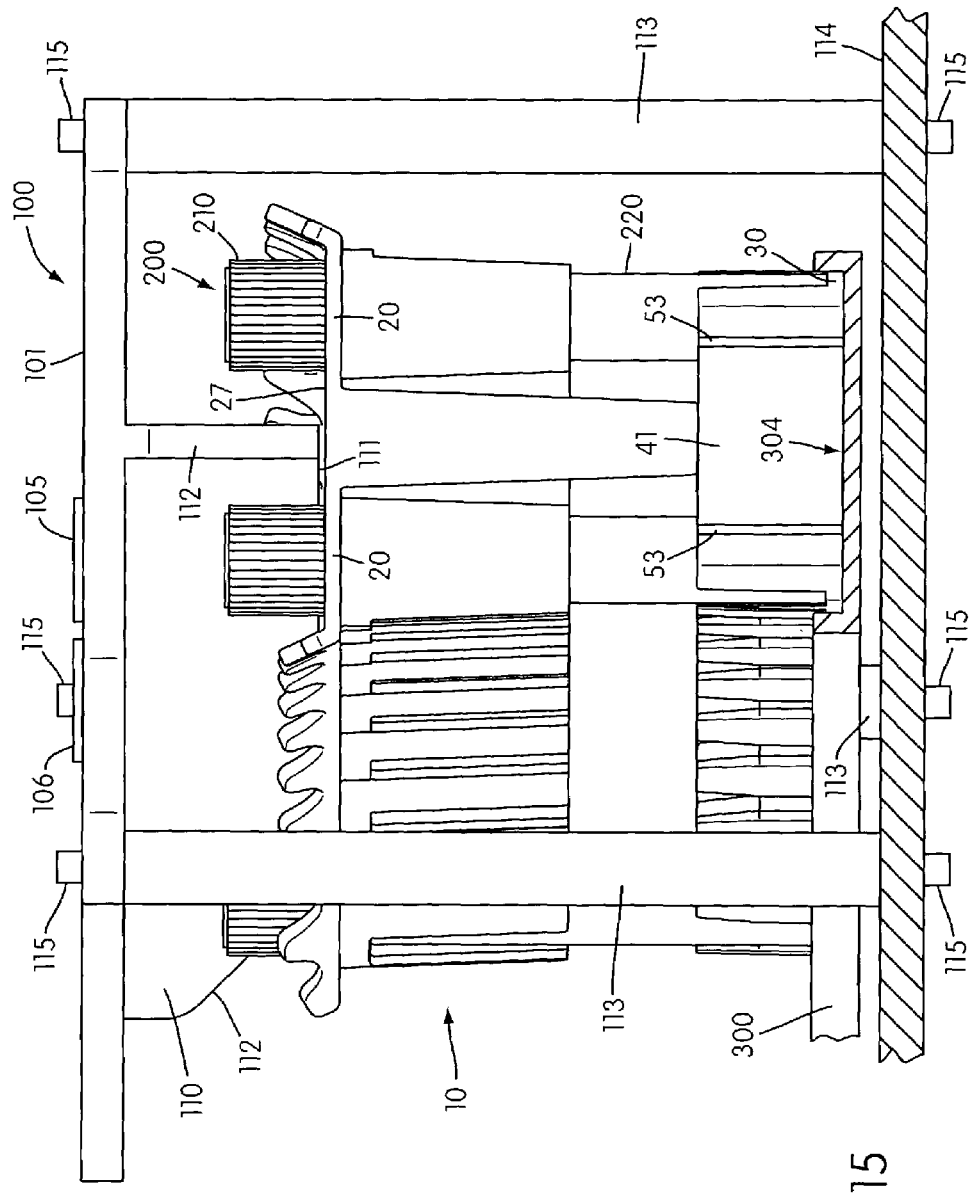
FIG. 15 is a section end view of the sample carrier of FIG. 1 carried under the drip shield of FIG. 11 by the sample carousel of FIG. 10.

When the drip shield 100 is employed in an automated sampling system, a bottom surface 109 of the drip shield preferably includes a depending fin 110, as illustrated in FIG. 12. The fin 110 is constructed and arranged on the bottom surface 109 of the drip shield 100 to limit vertical movement of the sample carrier under the drip shield, as illustrated in FIG. 15. Vertical movement of the sample carrier 10 is of particular concern when a robotic pipettor is used to withdraw test sample from sample tubes 200 having penetrable caps 210. Depending on the withdrawal force required, it may be possible for a pipette tip mounted on a robotic pipettor to become snagged on the penetrable components of the cap 210 as the pipette tip is being withdrawn from the sample tube 200. As a consequence, a portion of the sample carrier 10 may be lifted from, and possibly relocated on, the sample carrousel 300 by the robotic pipettor. Therefore, to limit vertical movement of the sample carrier 10 under the sample shield 200, the distance between a bottom surface 111 of the fin 110 and the top surface 27 of the top wall 20 of the sample carrier is less than the vertical distance needed to extract or displace at least a portion of the sample carrier from its location on the sample carousel 300 (e.g., less than the depth of the sample carousel receiving well 304). Vertical relocation of a sample tube 200 may occur when the retention force of a sample tube 200 (i.e., the cap component 210) applied to a pipette tip being withdrawn from the sample tube exceeds the holding force of the spring 60 applied to the sample tube. Preferably, the distance between the bottom surface 111 of the fin 110 and the top surface 27 of the top wall 20 of the sample carrier 10 is no more than about 0.125 inches (3.18 mm). The fin 110 can also function as a barrier to carryover contamination between sample tubes 200 held in sample tube holding areas 32 on opposite sides of the support wall 40 of the sample carrier 10. For that reason, the fin 110 is preferably longitudinally or arcuately centered on the bottom surface 109 of the cover plate 101.

The preferred fin 110 has tapered ends 112, as shown in FIG. 12. The tapered ends 112 are provided to facilitate proper seating of sample carriers 10 which have not been fully inserted into their corresponding sample carousel receiving wells 304 prior to rotation, whether the sample carousel 300 is being rotated clockwise or counterclockwise. The drip shield 100 can be maintained in fixed relationship over sample carriers 10 being indexed on the sample carousel 300 therebelow by means of mounting posts 113 fixed to a stationary surface 114 of the automated sampling system, as shown in FIG. 10 and more fully described by Ammann et al., U.S. Pat. No. 6,335,166. The drip shield 100 can be secured to these mounting posts 113 using screws, bolts or like mechanical fasteners. Preferred are bolts 115 mated with threaded holes (not shown) in the mounting posts 113 and inserted through three through-holes 116 located on the periphery of the drip shield 100, as shown in FIG. 10.

Sample carriers 10 and drip shields 100 of the present invention are preferably made of a substantially non-conductive plastic formed by any known injection molding procedure. Currently preferred is an injection molded acrylonitrile-butadiene-styrene plastic. To ensure more uniform curing of the molded components of the sample carrier, the top wall 20 includes a series of rectangular wells 28 depending into the upper portion 40A of the support wall 40, the base 30 includes a series of triangular cavities 36 extending into the Y-shaped dividers 34 on each side of the support wall, and the base includes a series of rectangular wells 37 extending into the lower portion 40A of the support wall.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

We claim:

1. A sample carrier for use in holding and centering a plurality of sample tubes for access by a robotic pipetting device, the sample carrier comprising:
    a top wall having a plurality of spaced-apart openings, each opening being dimensioned to receive one of a plurality of sample tubes therethrough;
    a plurality of sleeves, each sleeve depending from a bottom surface of the top wall and circumscribing one of the openings, each sleeve having an inner surface dimensioned to receive a vessel component of one of the sample tubes therethrough, and each sleeve having an opening configured and arranged to permit viewing of a label affixed to one of the sample tubes;
    a base defining a plurality of sample tube holding areas, each sample tube holding area corresponding to one of the openings and having one or more upwardly extending retaining walls opposite the support wall for holding one of the sample tubes in a substantially fixed, vertical orientation below the corresponding opening;
    a support wall joining the top wall and the base; and
    a plurality of springs extending outward from the support wall, each spring being associated with one of the sample tube holding areas, wherein the springs are configured and arranged so that each spring biases one of the sample tubes against the one or more retaining walls of the associated sample tube holding area.

2. The sample carrier of claim 1, wherein the top wail includes a series of the openings aligned along both sides of the support wall.

3. The sample cater of claim 1, wherein the openings are of the same or different sizes.

4. The sample carrier of claim 1 further comprising one or more of the sample tubes, each sample tube being present in one of the sample tube holding areas, wherein a cap component of at least one of the sample tubes is in touching contact with the inner surface of the corresponding sleeve.

5. The sample carrier of claim 1, wherein the openings are generally circular and the sleeves are generally cylindrical.

6. The sample carrier of claim 1, wherein the top wall has upwardly flared edges to facilitate handling of the sample carrier.

7. The sample carrier of claim 6, wherein the flared edges of the top wall include a plurality of recesses, each recess being adjacent one of the openings to provide finger access to sample tubes held by the sample carrier.

8. The sample carrier of claim 1 further comprising end walls joined to the base and a plurality of partitions, each partition extending radially or perpendicularly outward front the support wall and separating adjacent sample tube holding areas.

9. The sample carrier of claim 8, wherein each partition and a pair of retaining walls are joined to form a Y-shaped divider.

10. The sample carrier of claim 1, wherein each spring is a leaf spring.

11. The sample carrier of claim 10, wherein the springs are positioned between upper and lower portions of the support wall.

12. The sample carrier of claim 4, wherein the longitudinal axis of the cap component is within about 0.125 inches of the longitudinal axis of the corresponding opening.

13. The sample carrier of claim 4, wherein the longitudinal axis of the cap component is within about 0.1 inches of the longitudinal axis of the corresponding opening.

14. The sample carrier of claim 1, wherein the sample carrier has an arcuate shape.

15. A sample carrier for use in holding and centering a plurality of sample tubes for access by a robotic pipetting device, the sample carrier comprising:
a top wall having two sets of aligned, annular, spaced-apart openings, each opening being dimensioned to receive a sample tube therethrough;
a plurality of cylindrical sleeves, each sleeve depending from a bottom surface of the top wall and circumscribing one of the openings, each sleeve having an inner surface dimensioned to receive a vessel component of one of the sample tubes therethrough, and each sleeve having an opening configured and arranged to permit viewing of a label affixed to one of the sample tubes;
a base defining a plurality of sample tube holding areas, each sample tube holding area corresponding to one of the openings and having one or more upwardly extending retaining walls opposite the support wall for holding one of the sample tubes in a substantially fixed, vertical orientation below the corresponding opening;
a support wall joining the top wall and the base, wherein the sets of openings are positioned on opposite sides of the support wall; and
a plurality of leaf springs, each leaf spring having a pair of spring arms extending outward from opposite sides of the support wall, each spring arm being associated with one of the sample tube holding areas, wherein the leaf springs are configured and arranged so that each spring arm biases one of the sample tubes against the one or more retaining walls of the associated sample tube holding area.

16. The sample carrier of claim 15, wherein the top wall has upwardly flared edges to facilitate handling of the sample carrier.

17. The sample carrier of claim 16, wherein the flared edges of the top wall include a plurality of recesses, each recess being adjacent one of the openings to provide finger access to sample tubes held by the sample carrier.

18. The sample carrier of claim 15 further comprising lateral end walls joined to the base and a plurality of partitions, each partition extending radially or longitudinally outward from the support wall and separating adjacent sample tube holding areas.

19. The sample carrier of claim 18, wherein each partition and a pair of retaining walls are joined to form a Y-shaped divider.

20. The sample carrier of claim 15 further comprising one or more of the sample tubes, each sample tube being present in one of the sample tube holding areas, wherein a cap component of at least one of the sample tubes is in touching contact with the inner surface of the corresponding sleeve.

21. The sample carrier of claim 20, wherein the longitudinal axis of the cap component is within 0.125 inches of the longitudinal axis of the corresponding opening.

22. The sample carrier of claim 20, wherein the longitudinal axis of the cap component is within about 0.1 inches of the longitudinal axis of the corresponding opening.

23. The sample carrier of claim 15, wherein each leaf spring is positioned between upper and lower portions of the support wall.

24. The sample carrier of claim 15 wherein the sample carrier has an arcuate shape.

* * * * *